(12) United States Patent
Crawley

(10) Patent No.: US 6,190,853 B1
(45) Date of Patent: Feb. 20, 2001

(54) PHOTOGRAPHIC ELEMENTS CONTAINING NOVEL YELLOW COUPLERS

(75) Inventor: Michael W. Crawley, Watford (GB)

(73) Assignee: Eastman Kodak Company, Rochester, NY (US)

( * ) Notice: Under 35 U.S.C. 154(b), the term of this patent shall be extended for 0 days.

(21) Appl. No.: 09/388,161

(22) Filed: Sep. 1, 1999

(30) Foreign Application Priority Data

Sep. 19, 1998 (GB) .................................... 9820392

(51) Int. Cl.$^7$ ................. G03C 1/08; G03C 7/26; G03C 7/32
(52) U.S. Cl. ............... 430/557; 430/505; 430/544; 430/957
(58) Field of Search .................... 430/557, 544, 430/505, 957, 955

(56) References Cited

U.S. PATENT DOCUMENTS

| | | | |
|---|---|---|---|
| 3,933,500 | * | 1/1976 | Shiba et al. ............ 430/544 |
| 4,345,024 | * | 8/1982 | Hirano et al. .......... 430/544 |
| 5,116,717 | * | 5/1992 | Matsushita et al. ..... 430/544 |
| 5,451,493 | * | 9/1995 | Merkel et al. .......... 430/544 |
| 5,677,144 | | 10/1997 | Lussier et al. ......... 430/300 |
| 5,834,167 | | 11/1998 | Lussier et al. ......... 430/309 |

FOREIGN PATENT DOCUMENTS 2-262656  10/1990  (JP) .

* cited by examiner

Primary Examiner—Geraldine Letscher
(74) Attorney, Agent, or Firm—Arthur E. Kluegel

(57) ABSTRACT

This application discloses a photographic element comprising an image dye-forming coupler, and in particular a yellow coupler with an indazole coupling-off group which produces images with improved sharpness and comprises a light sensitive silver halide emulsion layer containing an image-dye-forming coupler of formula (I)

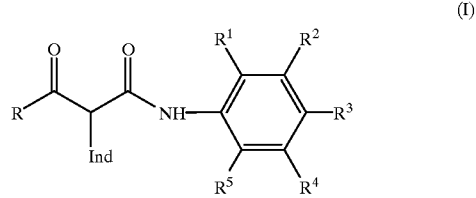

(I)

wherein:

R is an alkyl, aryl, alkoxy or heterocyclic group;

$R^1$–$R^5$ are hydrogen or an independently selected substituent, provided that $R^1$ and $R^2$, $R^2$ and $R^3$, $R^3$ and $R^4$ and $R^4$ and $R^5$ may represent fused cyclic groups;

Ind is an indazole of formula (II):

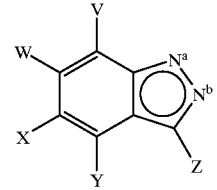

(II)

wherein

Ind is linked directly to the coupler via a ring nitrogen atom ($N^a$ or $N^b$); and V, W, X, Y and Z are the same or different and are hydrogen or a substituent;

provided that the sum of the Hammett sigma para values of V, W, X, Y and Z is equal to or greater than 0.4.

12 Claims, No Drawings

PHOTOGRAPHIC ELEMENTS CONTAINING NOVEL YELLOW COUPLERS

FIELD OF THE INVENTION

This invention relates to silver halide-based photographic elements containing yellow dye-forming couplers, hereinafter called yellow couplers. In particular, the invention relates to elements with yellow couplers with an indazole coupling-off group providing images with improved sharpness for use with silver halide based photographic emulsions.

BACKGROUND OF THE INVENTION

Photographic layers sensitive to blue light for use in a color photographic material typically contain a yellow coupler which, on reaction with an oxidised p-phenylenediamine developer, forms a yellow dye. Generally commercially available photographic films contain pivaloyl or benzoyl acetanilide yellow couplers. With such couplers a person skilled in the art will be aware that there will be usually have to be a compromise in choice of coupler between coupler activity as measured for example by contrast on the one hand and dye stability on the other.

It will be appreciated that it is a desirable feature of photographic systems to produce images which are not only correct in color, density and contrast and with satisfactory dye stability but which are also visually sharp. Currently this can be achieved by the use of a combination of an image coupler with a development inhibitor releasing coupler (DIR), from which inhibitor is released directly as a coupling-off group, or with a development inhibitor anchiameric releasing coupler (DIAR), from which inhibitor is released from a coupling-off group after a time delay which results from an additional reaction step. This delay permits control over such parameters as time of release, rate of release and rate of diffusion of the coupling-off group.

It would be advantageous to obtain visually sharp images, while retaining the other desired characteristics, by the use of a single coupler. The criterion for the success of this would be that the inhibitor fragment would be a mild inhibitor and that the coupler would have good activity. The two aspects would need to be carefully balanced to achieve the desired results giving good sensitometry for yellow image couplers, and in particular adequate activity for image formation, sufficient inhibition to give a noticeable improvement in image sharpness with no deleterious effects on dye stability and especially dark/wet stability.

SUMMARY OF THE INVENTION

According to the present invention there is provided a photographic element comprising a light sensitive silver halide emulsion layer containing an image-dye-forming coupler of formula (I):

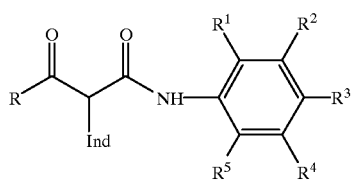

(I)

wherein:

R is an alkyl, aryl, alkoxy or heterocyclic group;

$R^1$–$R^5$ are hydrogen or an independently selected substituent, provided that $R^1$ and $R^2$, $R^2$ and $R^3$, $R^3$ and $R^4$ and $R^4$ and $R^5$ may represent fused cyclic groups;

Ind is an indazole of formula (II):

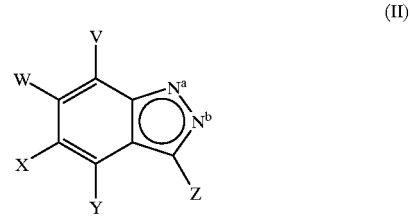

(II)

wherein

Ind is linked directly to the coupler via a ring nitrogen atom ($N^a$ or $N^b$); and V, W, X, Y and Z are the same or different and are hydrogen or a substituent;

provided that the sum of the Hammett sigma para values of V, W, X, Y and Z is equal to or greater than 0.4.

The present invention also includes the coupler compound of formula (I).

The elements of the invention exhibit improved sharpness and other desirable image qualities.

DETAILED DESCRIPTION OF THE INVENTION

The invention is as generally described in the Summary of the Invention. Substituent R is an alkyl, aryl, alkoxy or heterocyclic group. In particular, R is selected from an alkyl (including alkenyl), aryl, alkoxy or heterocyclic group optionally substituted with one or more coupler-modifying functional groups and is typically alkyl, alkoxy, phenyl, naphthyl, pyridyl or dioxanyl, preferably alkyl, alkoxy or phenyl, especially i-propyl, t-butyl, ethoxy or phenyl, optionally substituted with, for example, alkyl, alkoxy, chloro or alkylsulfamoyl.

Thus unsubstituted or substituted R may be selected from one of the following representative groups, without limitation thereto:

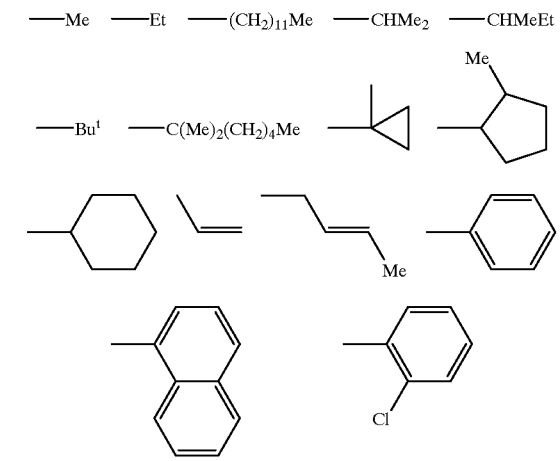

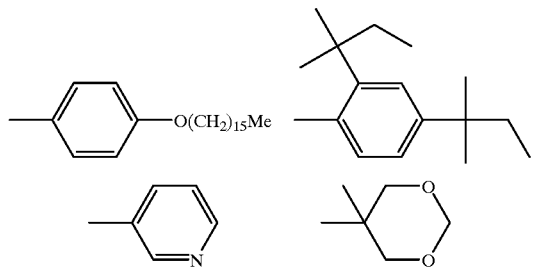

where $R^1$–$R^5$, are hydrogen or an independently selected substituent, provided that $R^1$ and $R^2$, $R^2$ and $R^3$, $R^3$ and $R^4$ and $R^4$ and $R^5$ may represent fused cyclic groups. Suitably, one or more of R or $R^1$–$R^5$ is selected from coupler-solubilizing groups, ballasting groups and dye hue-modifying groups. Photographic ballast groups are known in the art and comprise an organic group of such size and configuration so as to make the coupler molecule non-diffusible in a coated photographic element. Two or more couplers may be attached to the same ballast group or two or more ballasts may be attached to the same coupler. Generally the sum of the number of carbon atoms in one or more ballast groups is at least 10.

$R^1$–$R^5$ may be selected from hydrogen or a substituent, preferably one that is non-deleterious to the coupling reaction between the coupler and the oxidized developer. Examples of suitable substituents are, but not limited to, halogen, R, RO, $R_2$N, RHN, $H_2$N, RS, RSO, $RSO_2$NH, $RSO_2$, $RSO_2$O, ROOC, HOOC, RCOO, RNHCO, $R_2$NCO, RNHCONH, RCONH, $RNHSO_2$, $R_2NSO_2$, $H_2NSO_2$, RCO, $NO_2$, CN, $CF_3$, $P(OR)_3$, $PO(OR)_3$, where R is a group as above defined other than alkoxy. Substituents $R^1$ and $R^2$, $R^2$ and $R^3$, $R^3$ and $R^4$ and/or $R^4$ and $R^5$ may represent a fused cyclic group (e.g. $R^1$ and $R^2$ may represent the residue of a fused benzene or pyridine ring).

Preferably $R^1$–$R^5$ are selected from hydrogen, halogen, or substituted or unsubstituted alkoxy, aryloxy, carboxy ester, alkyl- or aryl-sulfonyl, alkyl- or aryl-carbamoyl, alkyl- or aryl-sulfonamido, alkyl- or aryl-sulfamoyl and alkyl- or aryl-sulfonyloxy. More preferably there are present at least two substituents on the phenyl ring of the anilide portion of the coupler and it is especially preferred that at least one of these is a chloro or alkoxy group in the ortho position on the phenyl ring.

Some representative examples of the aryl group attached to the anilide portion of the coupler (I) are shown below but suitable compounds are not limited to this list.

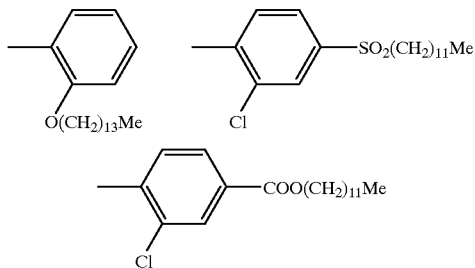

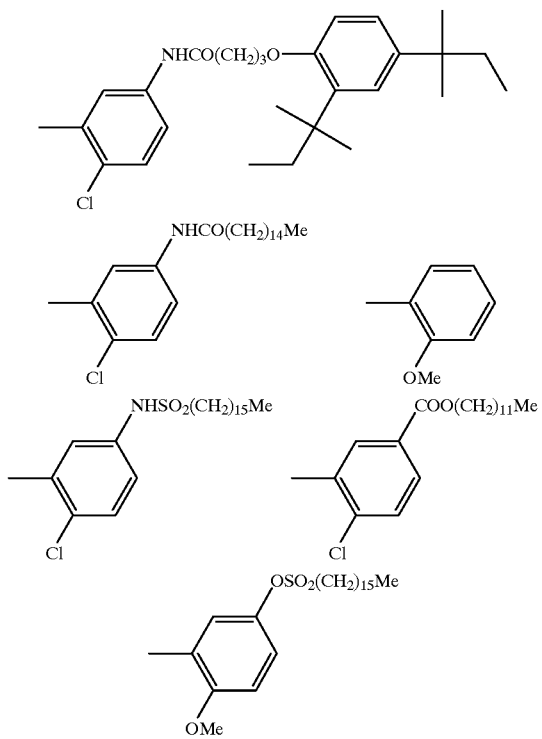

Moreover any of the above substituents $R^1$–$R^5$, other than H and halogen, may be substituted with one or more of the same or different substituents of $R^1$–$R^5$ as hereinabove defined, which may in turn be further substituted. Generally at least one of $R^1$–$R^5$ is or contains a ballast group although such a group may alternatively or additionally be present in the R substituent or in the indazole coupling-off group.

A coupler-modifying group is a substituent which, by its presence in the coupler structure, influences the photographic or physical properties of the coupler or the dye derived from the coupler.

As used herein and throughout the specification the term alkyl refers to an unsaturated or saturated straight or branched chain alkyl group (including alkenyl) having 1–20 atoms and includes cycloalkyl having 3–8 carbon atoms.

Thus, unless otherwise specifically stated, substituent groups usable on molecules herein include any groups, whether substituted or unsubstituted, which do not destroy properties necessary for photographic utility. When the term "group" is applied to the identification of a substituent containing a substitutable hydrogen, it is intended to encompass not only the substituent's unsubstituted form, but also its form further substituted with any group or groups as herein mentioned. Suitably, the group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl, or groups which may be further substituted, such as alkyl, including straight or branched chain alkyl, such as methyl, trifluoro-methyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentyl-phenoxy) ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)-acetamido, alpha-(2,4-di-t-pentylphenoxy) butyramido, alpha-(3-pentadecylphenoxy)hexanamido, alpha-(4-hydroxy-3-t-butylphenoxy)tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxy-carbonylamino, phenoxycarbonylamino, benzyloxy-carbonylamino, hexadecyloxycarbonylamino, 2,4-di-t-butylphenoxycarbonylamino, phenylcarbonylamino, 2,5-(di-t-pentylphenyl)carbonylamino, p-dodecyl-phenylcarbonylamino, p-toluylcarbonylamino, N-methylureido, N,N-dimethylureido, N-methyl-N-dodecylureido, N-hexadecylureido, N,N-dioctadecyl-ureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentyl-phenyl)-N'-ethylureido, and t-butylcarbonamido; sulfonamido, such as methylsulfonamido, benzene-sulfonamido, p-toluylsulfonamido, p-dodecylbenzene-sulfonamido, N-methyltetradecylsulfonamido, N,N-di-propylsulfamoylamino, and hexadecylsulfonamido; sulfamoyl, such as N-methylsulfamoyl, N-ethyl-sulfamoyl, N,N-dipropylsulfamoyl, N-hexadecyl-sulfamoyl, N,N-dimethylsulfamoyl; N-[3-(dodecyloxy)-propyl]sulfamoyl, N-[4-(2,4-di-t-pentylphenoxy)butyl]-sulfamoyl, N-methyl-N-tetradecylsulfamoyl, and N-do-decylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetra-decylcarbamoyl, and N,N-dioctylcarbamoyl; acyl, such as acetyl, (2,4-di-t-amylphenoxy)acetyl, phenoxy-carbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecy-loxycarbonyl; sulfonyl, such as methoxysulfonyl, octyloxysulfonyl, tetradecyloxysulfonyl, 2-ethylhexyl-oxysulfonyl, phenoxysulfonyl, 2,4-di-t-pentylphenoxy-sulfonyl, methylsulfonyl, octylsulfonyl, 2-ethylhexyl-sulfonyl, dodecylsulfonyl, hexadecylsulfonyl, phenyl-sulfonyl, 4-nonylphenylsulfonyl, and p-toluylsulfonyl; sulfonyloxy, such as dodecylsulfonyloxy, and hexa-decylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenyl-sulfmyl, and p-toluylsulfinyl; thio, such as ethyl-thio, octylthio, benzylthio, tetradecylthio, 2-(2,4-di-t-pentylphenoxy) ethylthio, phenylthio, 2-butoxy-5-t-octylphenylthio, and p-tolylthio; acyloxy, such as acetyloxy, benzoyloxy, octadecanoyloxy, p-dodecyl-amidobenzoyloxy, N-phenylcarbamoyloxy, N-ethyl-carbamoyloxy, and cyclo-hexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzo-thiazolyl; quaternary ammonium, such as triethyl-ammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. Generally, the above groups and substituents thereof may include those having up to 48 carbon atoms, typically 1 to 36 carbon atoms and usually less than 24 carbon atoms, but greater numbers are possible depending on the particular substituents selected.

The coupling-off group, Ind, is a substituted indazole inhibitor fragment of formula (II), wherein the sum of the sigma Hammett's sigma para values of these substituents is equal to or greater than 0.4, preferably greater than 0.6. At least one of these substituents is preferably a nitro group, although other suitable electron-withdrawing groups include cyano, halogen, alkyl- or aryl-sulfonyl, alkyl- or aryl-sulfonamido and alkyl- or aryl-oxycarbonyl.

Some examples of the formula (II) are shown below, without limitation thereto.

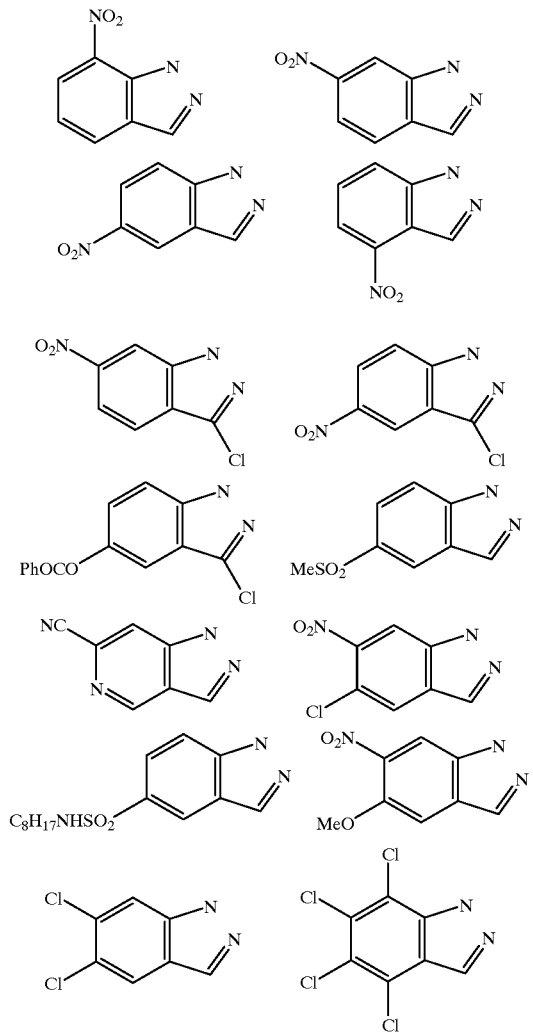

-continued
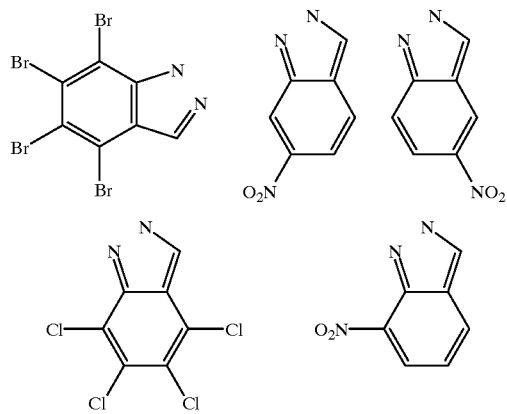
In some embodiments, the image-forming coupler may be selected from the following couplers:
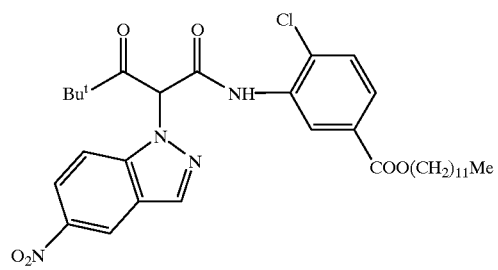
(C1)
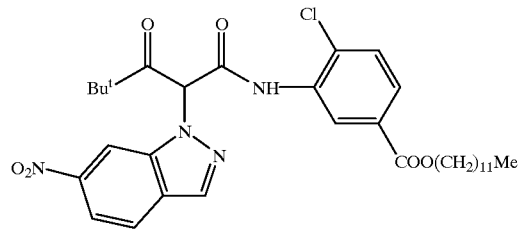
(C2)
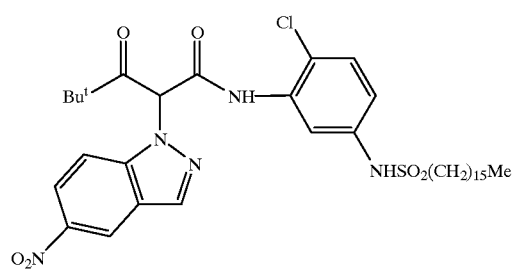
(C3)
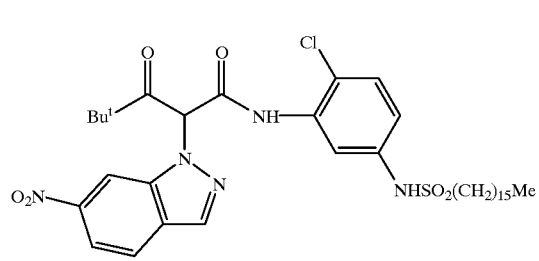
(C4)
-continued
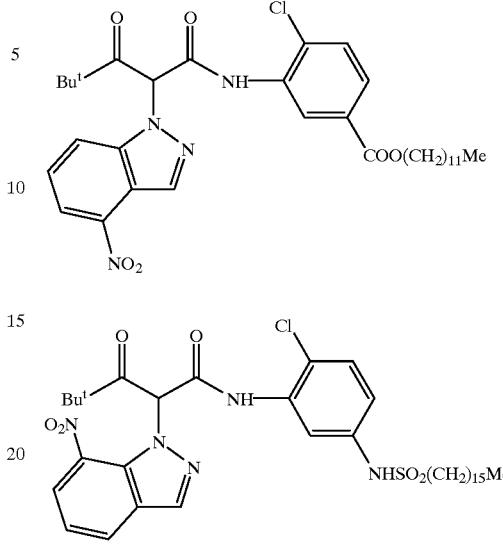
(C5)
(C6)
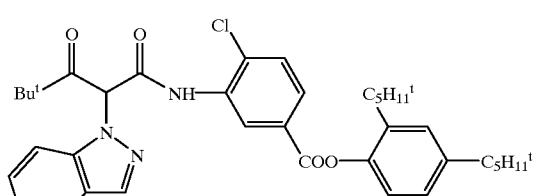
(C7)
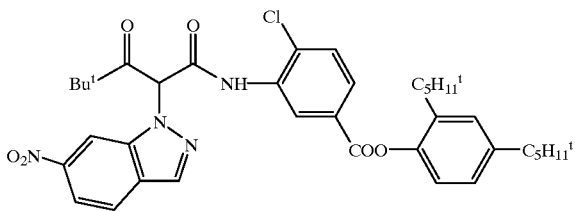
(C8)
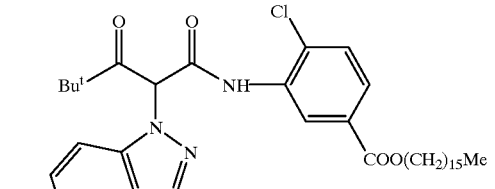
(C9)
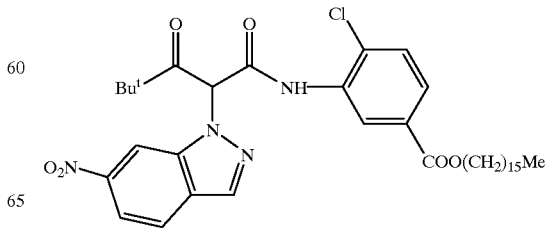
(C10)

-continued
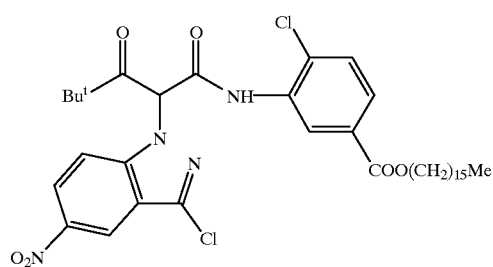
(C11)
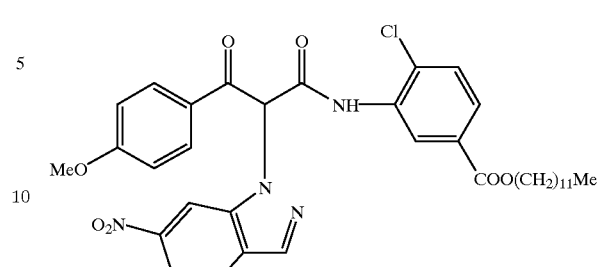
(C16)
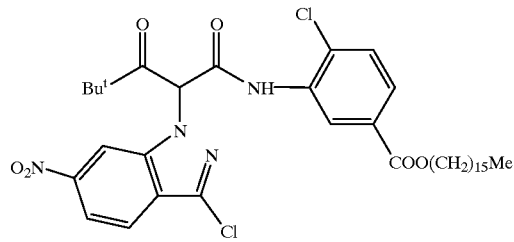
(C12)
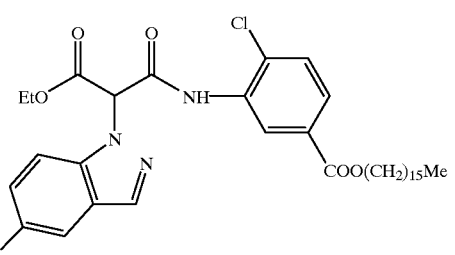
(C17)
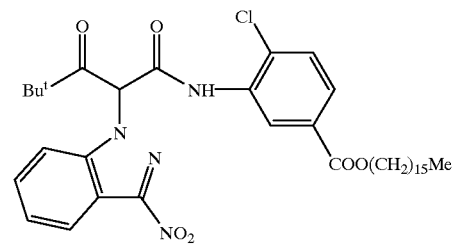
(C13)
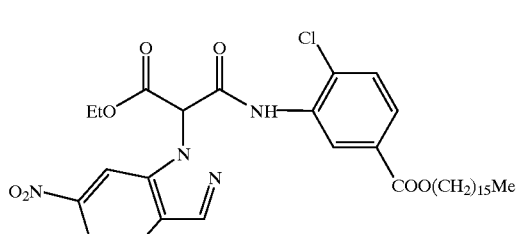
(C18)
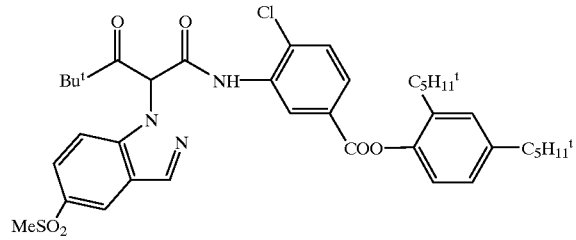
(C14)
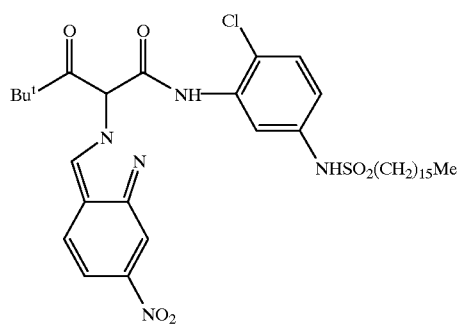
(C19)
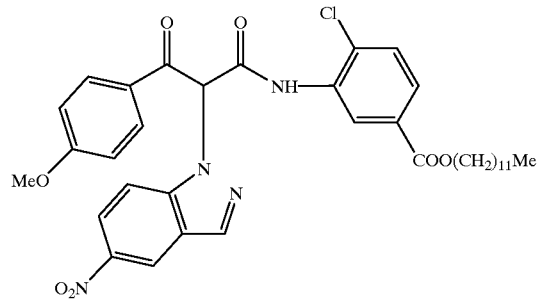
(C15)
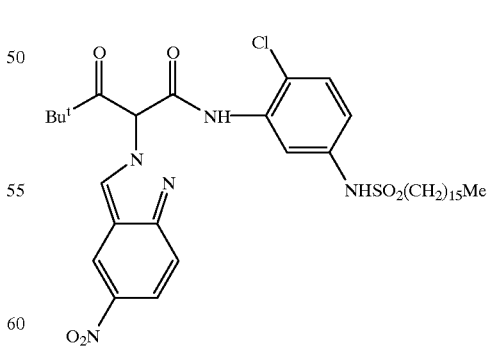
(C20)

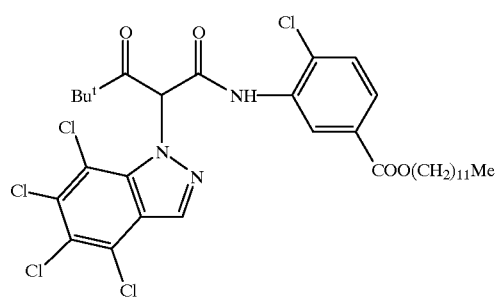
(C21)
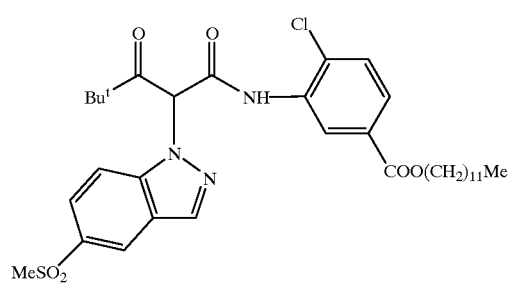
(C22)
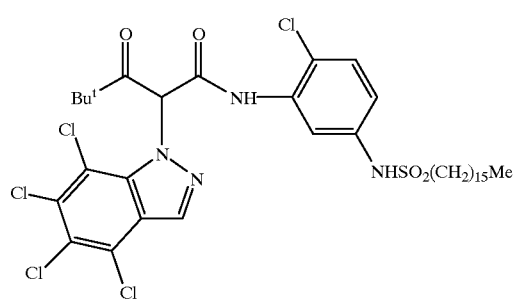
(C23)
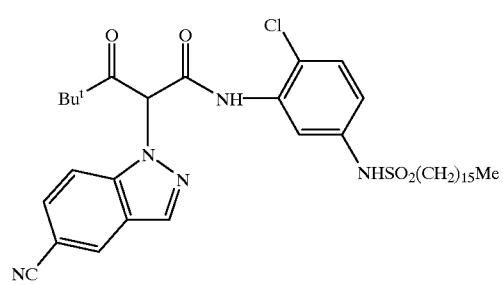
(C24)
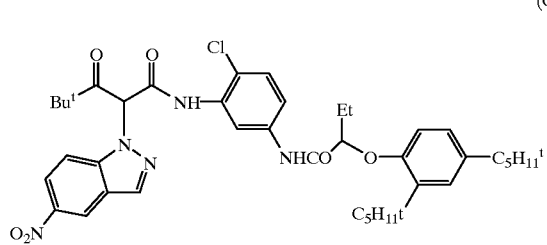
(C25)
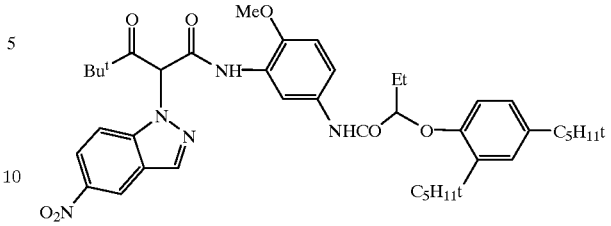
(C26)
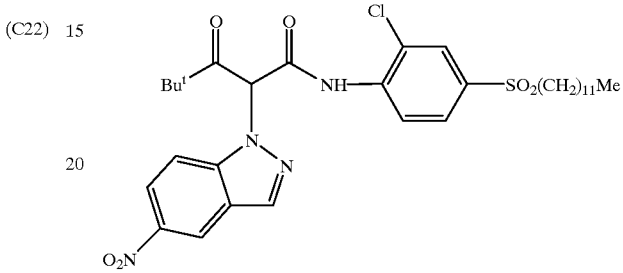
(C27)
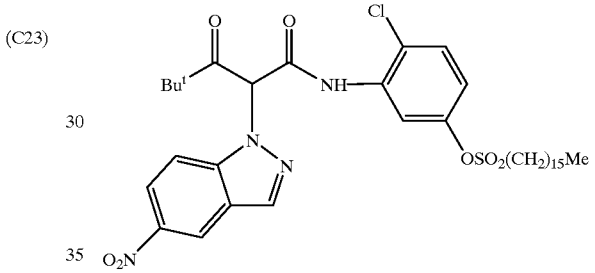
(C28)
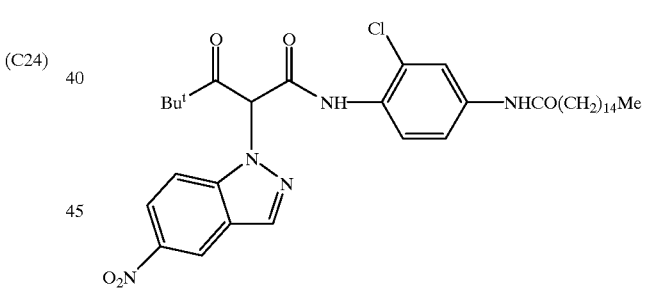
(C29)
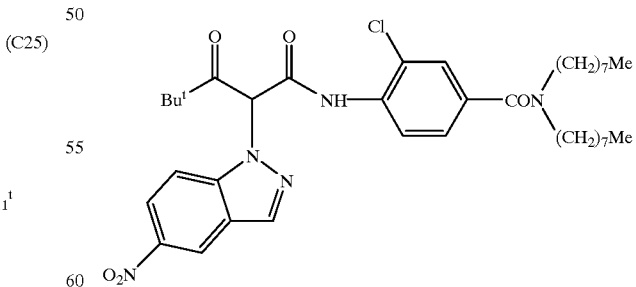
(C30)

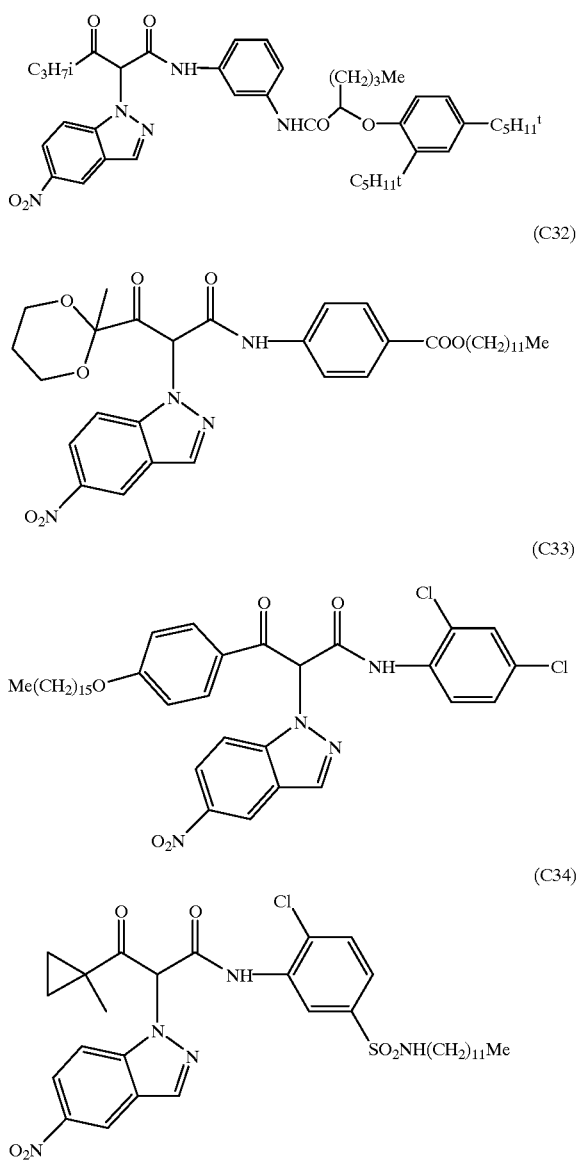

Couplers of the type represented by formula (I), in addition to their properties as DIR couplers, are capable of providing dyes with hue characteristics comparable to those obtained from other yellow image-dye-forming couplers in current use. In particular the dyes have low secondary absorptions in the green and red regions of the spectrum, narrow half-bandwidth and good dye stability, especially dark-wet stability. The couplers themselves have good raw-stock keeping properties and low continued coupling characteristics and are readily prepared from inexpensive precursors in a short number of steps giving advantages in the cost of manufacture. The released indazole coupling-off group in the coupler of formula (I) acts as a mild inhibitor, which is not strong enough to depress the coupling activity to an unusable level, but is sufficiently strong to have an effect on the image structure such that the improvement in image sharpness is observed.

The photographic element may be a single color element or a multicolor element. Multicolor elements contain image-dye-forming units sensitive to each of the three primary regions of the visible range of the electromagnetic spectrum. Each unit may comprise a single emulsion layer or a plurality of emulsion layers sensitive to a given region of the spectrum. The layers of the element, including the layers of the image-dye-forming units, may be arranged in various orders as known in the art. In an alternative format, the emulsions sensitive to each of the three primary regions of the spectrum may be disposed as a single segmented layer.

A typical multicolor photographic element comprises a support bearing a cyan image-dye-forming unit comprising a red-sensitive silver halide emulsion layer and a cyan dye-forming coupler, a magenta image-dye-forming unit comprising at least one green-sensitive silver halide emulsion layer and a magenta dye-forming coupler, a yellow image-dye-forming unit comprising at least one blue-sensitive silver halide emulsion layer and a yellow dye-forming coupler. The element may contain additional layers, such for example as filter layers, interlayers, overcoat layers and subbing layers.

If desired, the photographic element can be used in conjunction with an applied magnetic layer as described in Research Disclosure, November 1992, Item 34390 published by Kenneth Mason Publications, Ltd., Dudley Annex, 12a North Street, Emsworth, Hampshire P010 7DQ, England, the contents of which are incorporated herein by reference. When it is desired to employ the inventive materials in a small format film, Research Disclosure, June 1994, Item 36230, provides suitable embodiments.

In the following discussion of suitable materials for use in the emulsions and elements of this invention, reference will be made to Research Disclosure, September 1994, item 36544, available as described above, which will be identified hereafter by the term "Research Disclosure". The contents of the Research Disclosure, including the patents and publications referenced therein, are incorporated herein by reference and the Sections hereafter referred to are Sections of the Research Disclosure.

The silver halide emulsions employed in the elements of this invention can be either negative-working or positive-working. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through IX. Color materials are described in Sections X through XIII. Scan facilitating is described in Section XIV. Supports, exposure, development systems, and processing methods and agents are described in Sections XV to XX. Certain desirable photographic elements and processing steps are described in Research Disclosure, Item 37038, February 1995.

With negative working silver halide a negative image may be formed. Optionally a positive (or reversal) image may be formed.

The color developing agent may be selected from p-phenylenediamines; typically the agent may be selected from:

4-amino-N,N-diethylaniline hydrochloride,
4-amino-3-methyl-N,N-diethylaniline hydrochloride,
4-amino-3-methyl-N-ethyl-N-(2-methanesulfonamidoethyl)aniline sesquisulfate hydrate,
4-amino-3-methyl-N-ethyl-N-(2-hydroxyethyl)aniline sulfate,
4-amino-3-(2-methanesulfonamido ethyl)-N,N-diethyl-aniline hydrochloride and 4-amino-N-ethyl-N-(2-methoxyethyl)-m-toluidine di-p-toluene sulfonic acid.

The yellow coupler in accordance with the invention may be used in combination with other classes of image couplers such as 3-acylamino- and 3-anilino-5-pyrazolones and heterocyclic couplers (e.g. pyrazoloazoles) such as, for example, those described in EP 285,274, U.S. Pat. No. 4,540,654 and EP 119,860; and other 5-pyrazolone couplers containing different ballasts or coupling-off groups such as, for example, those described in U.S. Pat. No. 4,301,235, U.S. Pat. No. 4,853,319 and U.S. Pat. No. 4,351,897. Yellow or cyan colored couplers (e.g. to adjust levels of interlayer correction) and/or masking couplers such as, for example, those described in EP 213,490, Japanese Published Application 58-172,647, U.S. Pat. No. 2,983,608, German Application DE 2,706, 117C, U.K. Patent 1,530,272, Japanese Application A-113935, U.S. Pat. No. 4,070,191 and German Application DE 2,643,965 may also be used. Said masking couplers may be shifted or blocked.

Photographically useful coupling-off groups are well-known in the art. Such groups can determine the equivalency of the coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, development acceleration or inhibition, bleach acceleration or inhibition, electron transfer facilitation and color correction.

Representative classes of coupling-off groups include halo, alkoxy, aryloxy, heterocyclyloxy, sulfonyloxy, acyloxy, acyl, heterocyclyl, sulfonamido, mercaptotetrazole, mercaptopropionic acid, phosphonyloxy, arylthio, and arylazo. These coupling-off groups are described in the art, for example, in U.S. Pat. Nos. 2,455,169, 3,227,551, 3,432,521, 3,476,563, 3,617,291, 3,880,661, 4,052,212 and 4,134,766; and in U.K. Patents and published application Nos. 1,466,728, 1,531,927, 1,533,039, 2,006,755A and 2,017,704A, the disclosure of which are incorporated herein by reference.

Thus, the coupler of the present invention may be used in association with materials that accelerate or otherwise modify the processing steps e.g. of bleaching or fixing to improve the quality of the image. Bleach accelerators described in EP 193,389; EP 301,477; U.S. Pat. No. 4,163,669; U.S. Pat. No. 4,865,956; and U.S. Pat. No. 4,923,784 are particularly useful. Also contemplated is use of the coupler in association with nucleating agents, development accelerators or their precursors (U.K. Patent 2,097,140; U.K. Patent 2,131,188; electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The yellow coupler may be used in combination with filter dye layers comprising colloidal silver sol or yellow and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. No. 4,420,556; and U.S. Pat. No. 4,543,323). Also, the couplers may in some embodiments be blocked or coated in protected form as described, for example, in Japanese Application 61/258,249 or U.S. Pat. No. 5,019,492.

The yellow coupler may further be used in combination with image-modifying compounds such as "Developer-Inhibitor-Releasing" compounds (DIR's); DIR's useful in conjunction with said couplers are known in the art and examples are described in U.S. Pat. Nos. 3,137,578; 3,148,022; 3,148,062; 3,227,554; 3,384,657; 3,379,529; 3,615,506; 3,617,291; 3,620,746; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346,899; 362,870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Color Photography", C. R. Barr. J. R. Thirtle and P. W. Vittum in Photographic Science and Engineering, Vol.13, p.174 (1969), incorporated herein by reference.

Generally, the developer inhibitor-releasing (DIR) couplers may include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzo-thiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptothiatriazoles, mercaptotriazoles, mercaptooxadiazoles, mercaptodiazoles, mercaptooxathiazoles, tellurotetrazoles or benzisodiazoles.

The invention will now be described with reference to, but not limited by, the following example and photographic data.

EXAMPLE OF SYNTHESIS OF COUPLERS OF FORMULA (I)

Preparation of Couplers (C3) and (C19)

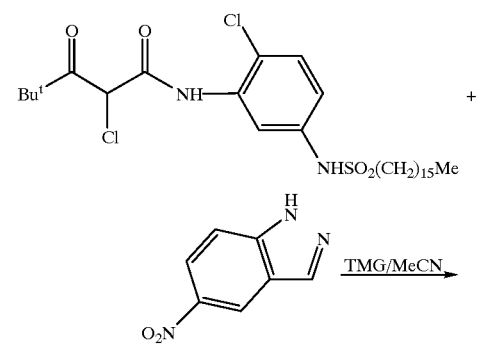

-continued

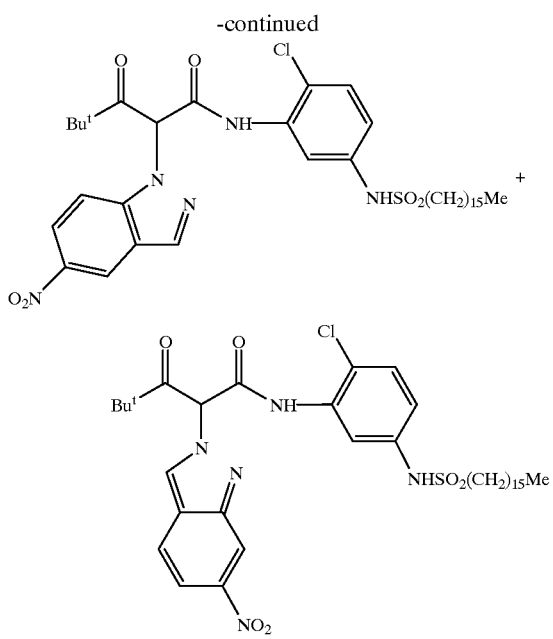

The starting materials are commercially available or readily prepared from known precursors by methods well known in the art.

N-(2-chloro-5-hexadecylsulphamoylphenyl)-2-chloro-3-keto-4,4-dimethylpentanoamide (11.82 g, 20 mmol) was dissolved in acetonitrile (100 ml) and 5-nitroindazole (3.26 g, 20 mmol) added. Tetramethylguanidine (TMG) (4.6 g, 40 mmol) was added dropwise with stirring over 10 min. and the mixture stirred for 2 h at ambient temperature. Thin layer chromatography (2:1 60–80° C. petroleum ether:ethyl acetate/silica gel) indicated that the reaction was complete and that two products had been formed. The mixture was poured into dilute hydrochloric acid (10%, 1 l) and the oily solid extracted into ethyl acetate, washed with dilute sodium carbonate (10%, 2×0.5 l), water and then dried ($MgSO_4$). Removal of the solvent gave a yellow oil which was chromatographed on a silica gel column using 2:1 60–80° C. petroleum ether:ethyl acetate as the eluent. The major fraction was isolated as a pale yellow solid (11.2 g) which was crystallised from 60–80° C. petroleum ether containing a little ethyl acetate to give pure coupler (3) as a white crystalline solid, 8.0 g, 56%. Spectral data (NMR,MS,IR) were consistent with the proposed structure.

$C_{36}H_{52}ClN_5O_6S$ Requires: C 60.2%, H 7.3%, N 9.75%
Found: C 60.1%, H 7.1%, N 9.6%

Further elution of the column afforded a small amount of pale yellow solid which was slurried with ethyl acetate and filtered to give a white solid identified as the isomeric coupler (19), 0.4 g, 3%. Spectral data (NMR,MS,IR) were consistent with the proposed structure.

$C_{36}H_{52}ClN_5O_6S$ Requires: C 60.2%, H 7.3%, N 9.75%
Found: C 60.0%, H 7.2%, N 9.8%

Couplers (4),(6)–(10),(15),(16), and (20) were prepared similarly.

Photographic Data (I) Test Procedures

Compounds of the present invention (and comparison compounds) were dispersed in coupler solvent and incorporated into photographic coatings containing a silver bromoiodide emulsion, on a transparent support, according to the following coating diagram:

| Gel Supercoat | |
|---|---|
| Gelatin | 1.50 g/m² |
| Emulsion Layer | |
| Silver bromoiodide | 0.81 g/m² |
| Bis(vinylsulphonyl) Coupler | 1.932 mmol/m² |
| Gelatin | 2.42 g/m² |
| Bis (vinylsulfonylmethane (hardener) | 0.06 g/m² |
| Support    Cellulose acetate | |

Aqueous dispersions of the couplers were prepared by methods known in the art. The yellow dye-forming coupler dispersions contained 6% by weight of gelatin, 9% by weight of coupler and a 1.0:0.5:1.5 weight ratio of coupler to di-n-butyl phthalate coupler solvent to cyclohexanone auxiliary solvent. The auxiliary solvent was included to aid in dispersion preparation and was removed by washing the dispersion for 6 hours at 4° C. and pH 6.0.

(i) Sensitometric testing

The experimental photographic coatings prepared in this way were slit and chopped into 30 cm×35 mm test strips. After hardening the strips were exposed (1.0 sec.) through a 0–4.0 neutral density step wedge (0.2 ND step increments) and Daylight V, Wratten 35+38A filters and 0.3 ND filter then processed through a standard C-41 process as described in the British Journal of Photography Annual (1988) 196–198 using the following steps and process times:

| Developer | 2.5 min. |
|---|---|
| Bleach | 4.0 min. |
| Wash | 2.0 min. |
| Fix | 4.0 min. |
| Wash | 2.0 min. |

For each test strip, Status M densities were measured as a function of exposure using a spectral array automatic transmission densitometer. Measurements of sensitometric parameters—minimum density ($D_{min}$), maximum density ($D_{max}$), contrast (γ) and photographic speed (KIT)—were obtained from plots of density vs. log exposure (DlogE curves).

In addition to the above standard conditions, separate strips of each coating were also developed in a competing process employing the same process steps as above but using a developer modified by the addition of 5.0 g/l citrazinic acid (CZA) and adjusted to pH 10.0 by the addition of sodium carbonate. The ratio of contrast in the competing process to contrast in the standard process (γCZA/γSTD) is quoted as an indication of in-film reactivity of the coupler.

(ii) Spectrophotometric testing 35 mm Test strips were exposed as above through a 0–0.9 ND step-wedge (0.3 ND increments) and Daylight V, Wratten 35+38A filters and the correct ND filters to give an optical density of ca. 1.0. The strips were processed using the standard conditions described above and samples cut from the yellow dye image step with density closest to 1.0. Visible absorption spectra of the resultant yellow dyes (normalised to 1.0 density) were obtained using a Pye-Unicam SP8-100 spectrophotometer. Dye hues are expressed in terms of the wavelength corresponding to the maximum absorption peak (λmax) and the width of the curve at half the peak height (half-bandwidth) (HBW).

(iii) Dye stability testing

Yellow dye sample patches of density ca. 1.0 were prepared as for spectrophotometric testing and their absorption spectra measured as above.

Dark/wet stability testing: The dye sample patches were incubated in a dark oven for periods of 1,3 and 6 weeks accumulated fade at a constant 60° C. and 70% relative humidity.

The spectrophotometric curves were re-measured after each fade period and the degree of fade quoted as the decrease in density at the wavelength of maximum absorption (λmax) relative to an initial normalised density of 1.0.

(II) Tabular Data

The data in Table 1 shows a comparison of the sharpness (MTF) (Modulation Transfer Function) of the images obtained from two of the couplers of the invention with that from the comparison couplers CC1 and CC2. As can be seen from the data the couplers of the invention show figures that are 1.5–4.0 higher in DMT units (descriptors of MTF units) than the comparison couplers, an increase of 1 DMT unit being considered to be a noticeable difference in sharpness.

TABLE 1

Sharpness (MTF) Measurements for Nitroindazole-Containing Couplers

| Coupler | MTF* (DMT units) |
| --- | --- |
| CC1 | 33.5 |
| CC2 | 34.0 |
| C3 | 37.5 |
| C4 | 35.5 |

*40% modulation, 35 mm format

Comparison Image Couplers

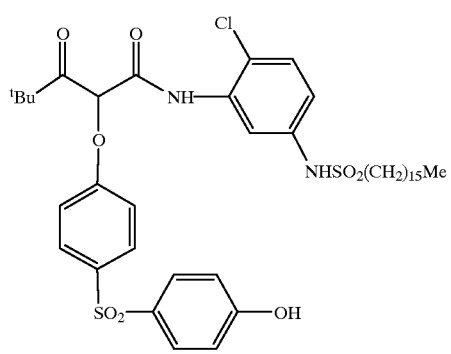
(CC1)

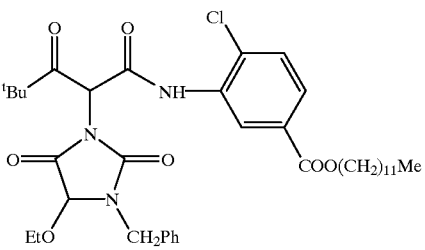
(CC2)

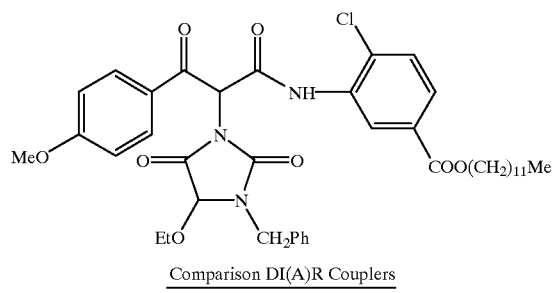
(CC3)

Comparison DI(A)R Couplers

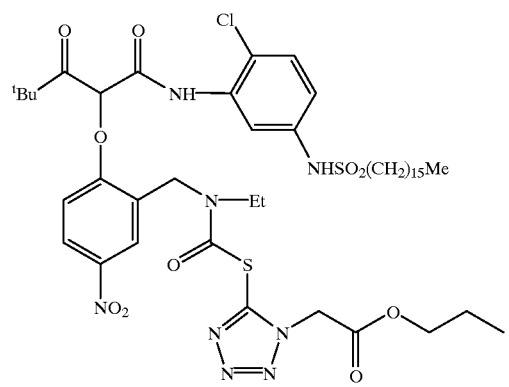
(CC4)

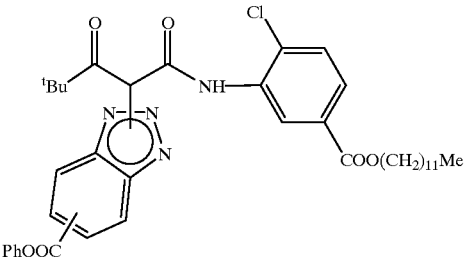
(CC5)

The data in Table 2 compares the sensitometry for examples of couplers of the invention with that of comparison image couplers CC1, CC2 and CC3. This data shows that the sensitometry of couplers of the invention enables them to be used as image couplers and in particular that the λmax and dye hues are in the usable range of the spectrum for these couplers. Comparison couplers CC4 and CC5 are typical DIR couplers. These compounds give little dye under the same processing conditions.

TABLE 2

Sensitometry for Nitroindazole Containing Couplers

| Coupler Number | $D_{max}$ | $D_{min}$ | γ | λmax-nm | HBW-nm |
|---|---|---|---|---|---|
| CC1 | 2.46 | 0.09 | 2.12 | 447.5 | 93.5 |
| CC2 | 2.15 | 0.08 | 1.70 | 447.0 | 88.0 |
| CC3 | 2.86 | 0.11 | 2.77 | 448.0 | 90.0 |
| C3 | 1.97 | 0.09 | 1.33 | 447.5 | 90.0 |
| C4 | 2.09 | 0.09 | 1.79 | 447.0 | 95.0 |
| CC1 | 2.62 | 0.11 | 2.37 | 447.0 | 92.5 |
| CC2 | 2.10 | 0.10 | 1.57 | 446.5 | 87.5 |
| CC3 | 2.96 | 0.13 | 2.78 | 449.5 | 90.0 |
| CC4 | 0.76 | 0.08 | 0.39 | 449.0 | 86.5 |
| CC5 | 0.68 | 0.08 | 0.34 | 447.0 | 85.0 |
| C3 | 2.02 | 0.10 | 1.48 | 447.0 | 95.0 |
| C4 | 2.19 | 0.10 | 1.88 | 446.5 | 94.0 |
| C7 | 1.45 | 0.10 | 1.06 | 448.0 | 86.5 |
| C8 | 1.90 | 0.09 | 1.51 | 449.5 | 88.5 |
| C9 | 1.60 | 0.09 | 1.21 | 446.5 | 86.0 |
| C10 | 2.13 | 0.10 | 1.77 | 446.5 | 89.5 |
| C15 | 2.33 | 0.22 | 2.33 | 450.0 | 96.0 |
| C16 | 1.76 | 0.14 | 1.83 | 448.5 | 95.5 |

The data in Table 3 shows the dark wet stability of couplers of the invention compared to the comparison couplers CC1, CC2 and CC3 showing that the stability is at least as good as, and in many cases considerably superior to the comparison couplers.

TABLE 3

Dye Stability Data for Couplers and Controls

| Coupler Number | Dark/Wet Fade 6Wk - loss from 1.0 |
|---|---|
| CC1 | −0.02 |
| CC2 | −0.01 |
| CC3 | −0.20 |
| C3 | +0.01 |
| C4 | +0.03 |
| CC1 | −0.11 |
| CC2 | −0.01 |
| CC3 | −0.13 |
| C3 | +0.02 |
| C4 | +0.01 |
| C7 | −0.03 |
| C8 | −0.01 |
| C9 | −0.03 |
| C10 | −0.02 |
| C15 | −0.08 |
| C16 | −0.07 |

What is claimed is:

1. A photographic element comprising a light sensitive silver halide emulsion layer containing an image-dye-forming coupler of formula (I)

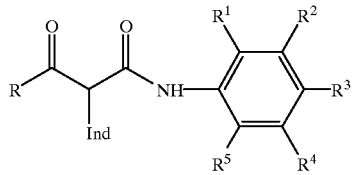

(I)

wherein:

R is an alkyl, aryl, alkoxy or heterocyclic group;

$R^1$–$R^5$ are hydrogen or an independently selected substituent, provided that $R^1$ and $R^2$, $R^2$ and $R^3$, $R^3$ and $R^4$ and $R^4$ and $R^5$ may represent fused cyclic groups;

Ind is an indazole of formula (II)

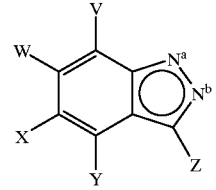

(II)

wherein

Ind is linked directly to the coupler via a ring nitrogen atom ($N^a$ or $N^b$); and V, W, X, Y and Z are the same or different and are hydrogen or a substituent;

provided that the sum of the Hammett's sigma para values of V, W, X, Y and Z is equal to or greater than 0.4.

2. The element of claim 1 wherein the sum of the Hammett's sigma para values of V, W, X, Y and Z is greater than 0.6.

3. The element of claim 1 wherein at least one of R and $R^1$–$R^5$ are selected independently from coupler-solubilizing groups, ballasting groups and dye hue-modifying groups.

4. The element of claim 3 wherein R and $R^1$–$R^5$ are selected so that the sum of the number of carbon atoms in one or more ballast groups is at least 10.

5. The element of claim 1 wherein R is selected from alkyl, alkoxy, phenyl, naphthyl, pyridyl and dioxanyl groups.

6. The element of claim 5 wherein R is selected from i-propyl, t-butyl, ethoxy and phenyl groups.

7. The element of claim 1 wherein $R^1$–$R^5$ are independently selected from hydrogen, halogen, alkoxy, aryloxy, carboxy ester, alkyl- or aryl-sulfonyl, alkyl- or aryl-carbamoyl, alkyl- or aryl-sulfonamido, alkyl- or aryl-sulfamoyl and alkyl- or aryl-sulfonyloxy groups.

8. The element of claim 7 wherein $R^1$ is selected from chloro and alkoxy.

9. The element of claim 1 wherein at least one of V, W, X, Y and Z is an electron-withdrawing group selected from nitro, cyano, halogen, alkyl-or aryl-sulfonyl, alkyl- or aryl-sulfonamido and alkyl- or aryl-oxycarbonyl groups.

10. The element of claim 9 wherein at least one of V, W, X, Y and Z is a nitro group.

11. The element of claim 1 wherein the coupler of formula (I) has one of the following formulae where Bu means butyl and Me means methyl:

(C3)
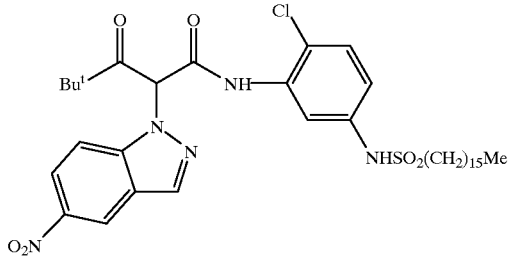

(C4)
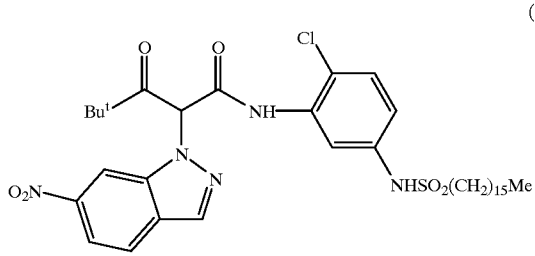

(C7)
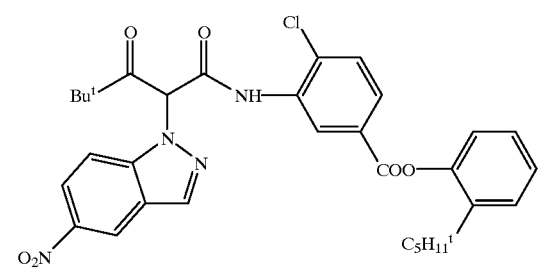

(C8)
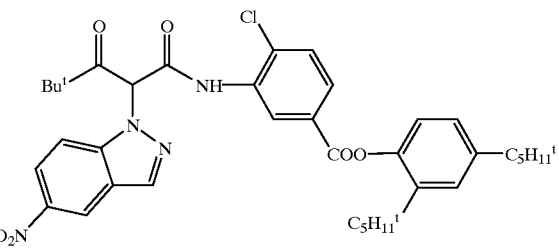

(C9)
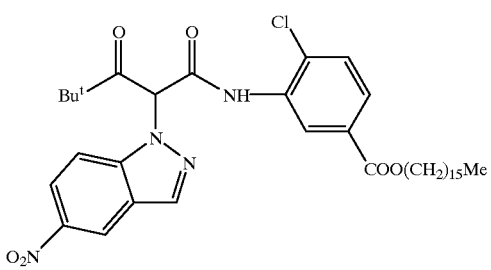

(C10)
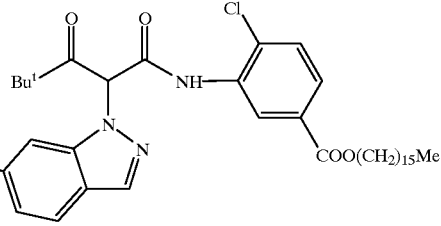

(C15)
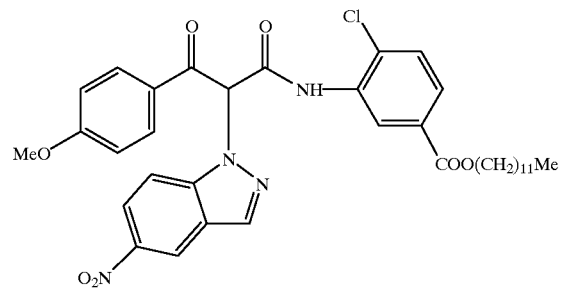

(C16)
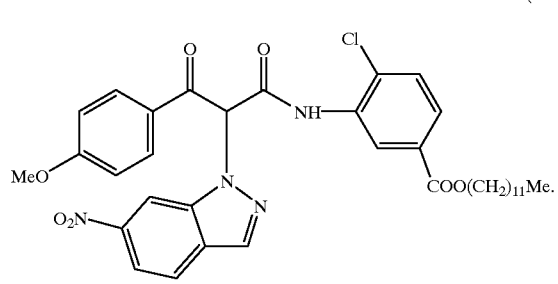

12. A multi-color photographic material comprising a support bearing yellow, magenta and cyan image-dye-forming units comprising at least one blue-, green- or red-sensitive silver halide emulsion layer having associated therewith at least one yellow, magenta or cyan dye-forming coupler respectively, comprising a light sensitive silver halide emulsion layer containing an image-dye-forming coupler of formula (I)

(I)
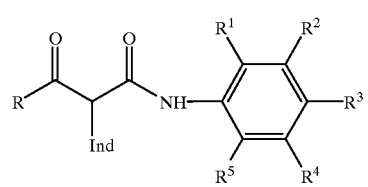

wherein:

R is an alkyl, aryl, alkoxy or heterocyclic group;

$R^1$–$R^5$ are hydrogen or an independently selected substituent, provided that $R^1$ and $R^2$, $R^2$ and $R^3$, $R^3$ and $R^4$ and $R^4$ and $R^5$ may represent fused cyclic groups;

Ind is an indazole of formula (II)
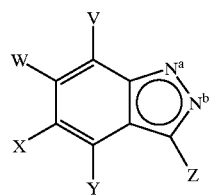
(II or Ind)
wherein
Ind is linked directly to the coupler via a ring nitrogen atom ($N^a$ or $N^b$); and
V, W, X, Y and Z are the same or different and are hydrogen or a substituent;
provided that the sum of the Hammett sigma para values of V, W, X, Y and Z is equal to or greater than 0.4.
* * * * *